US012751534B2

(12) United States Patent
Oh et al.

(10) Patent No.: US 12,751,534 B2
(45) Date of Patent: Oct. 6, 2026

(54) BEAUTY DEVICE

(71) Applicants: LG HOUSEHOLD & HEALTH CARE LTD., Seoul (KR); AMOGREENTECH CO., LTD, Gimpo-si (KR)

(72) Inventors: Sung Taek Oh, Seoul (KR); Sang Dong Jeong, Gimpo-si (KR); Jin Pyo Park, Gimpo-si (KR); Jung Yong Lee, Seoul (KR)

(73) Assignees: LG HOUSEHOLD & HEALTH CARE LTD., Seoul (KR); AMOGREENTECH CO., LTD, Gimpo-si (KR)

( * ) Notice: Subject to any disclaimer, the term of this patent is extended or adjusted under 35 U.S.C. 154(b) by 1069 days.

(21) Appl. No.: 17/743,612

(22) Filed: May 13, 2022

(65) Prior Publication Data

US 2022/0361644 A1 Nov. 17, 2022

(30) Foreign Application Priority Data

May 14, 2021 (KR) ........................ 10-2021-0062925

(51) Int. Cl.

*A45D 19/00* (2006.01)
*A61H 23/02* (2006.01)
*A61N 5/06* (2006.01)

(52) U.S. Cl.

CPC ............. *A45D 19/00* (2013.01); *A61H 23/02* (2013.01); *A61N 5/0617* (2013.01); *A45D 2019/0033* (2013.01)

(58) Field of Classification Search

CPC .................... A45D 19/00; A45D 44/00; A45D 2019/0033; A45D 2200/205; A61H 7/003; A61H 23/02; A61H 23/0254; A61H 2201/0153; A61H 2201/0157; A61H 2201/105; A61H 2201/5025; A61H 2201/5058; A61H 2205/021; A61H 2205/022; A61M 37/00; A61M 2037/0007; A61M 2205/051; A61M 2210/005; A61M 2210/04; A61M 2210/06; A61M 2210/0606; A61N 1/328; A61N 1/36014; A61N 5/0616; A61N 5/0617; A61N 5/067; A61N 2005/0626; A61N 2005/0644;

(Continued)

(56) References Cited

U.S. PATENT DOCUMENTS 4,930,504 A * 6/1990 Diamantopoulos .. A61N 5/0616 250/494.1
9,301,588 B2 * 4/2016 Eckhouse .............. A45D 26/00

(Continued)

FOREIGN PATENT DOCUMENTS

JP 2012-75543 A 4/2012
JP 2013-111390 A 6/2013

(Continued)

*Primary Examiner* — Timothy A Stanis
*Assistant Examiner* — Matthew D Ziegler
(74) *Attorney, Agent, or Firm* — Birch, Stewart, Kolasch & Birch, LLP

(57) ABSTRACT

A beauty device may include a main body and a head module detachable from the main body, wherein the head module may include at least one of a plurality of protrusions, a light-emitting part, an electrode part, a sensor, and a motor, and the sensor may include a proximity sensor.

16 Claims, 8 Drawing Sheets

(58) Field of Classification Search
CPC .... A61N 2005/0651; A61N 2005/0652; A61N 2005/0659; A61N 2005/0662
See application file for complete search history.

(56) References Cited

U.S. PATENT DOCUMENTS

| | | | | |
|---|---|---|---|---|
| 10,525,277 | B1 * | 1/2020 | Chau | A61N 1/325 |
| 11,318,323 | B2 * | 5/2022 | Hetz | A61N 5/0625 |
| 2002/0198575 | A1 * | 12/2002 | Sullivan | A61N 5/0616 607/91 |
| 2003/0149382 | A1 * | 8/2003 | Waller | A61H 7/006 601/137 |
| 2007/0239142 | A1 * | 10/2007 | Altshuler | A61B 18/203 606/9 |
| 2014/0222026 | A1 | 8/2014 | Tenenbaum et al. | |
| 2015/0224020 | A1 * | 8/2015 | Flyash | A61B 5/0531 601/46 |
| 2015/0305969 | A1 | 10/2015 | Giraud et al. | |
| 2016/0022399 | A1 * | 1/2016 | St. Anne | A61H 19/34 600/32 |
| 2018/0015299 | A1 | 1/2018 | Kawa | |
| 2018/0036553 | A1 * | 2/2018 | Shiibashi | A45D 20/12 |
| 2020/0093945 | A1 | 3/2020 | Jeong | |

FOREIGN PATENT DOCUMENTS

| | | | |
|---|---|---|---|
| JP | 2015-535457 | A | 12/2015 |
| JP | 3226151 | U | 4/2020 |
| JP | 2021-29442 | A | 3/2021 |
| KR | 20-0453811 | Y1 | 5/2011 |
| KR | 10-1202822 | B1 | 11/2012 |
| KR | 10-2014-0049550 | A | 4/2014 |
| KR | 10-1380620 | B1 | 4/2014 |
| KR | 10-1506685 | B1 | 3/2015 |
| KR | 10-2019-0077278 | A | 7/2019 |
| KR | 10-2021-0044035 | A | 4/2021 |
| KR | 10-2021-0047406 | A | 4/2021 |
| WO | WO 2017/150381 | A1 | 9/2017 |

* cited by examiner

BEAUTY DEVICE

CROSS-REFERENCE TO RELATED APPLICATIONS

This application claims priority to and the benefit of Korean Patent Application No. 10-2021-0062925, filed on May 14, 2012, the disclosure of which is incorporated herein by reference in its entirety.

TECHNICAL FIELD

The present disclosure relates to a beauty device used for the scalp, skin, and the like.

BACKGROUND

As people's interest in beauty has increased, not only cosmetics, makeup tools, etc. Are diversified, but also the types of beauty devices are also gradually increasing. In particular, in the past, in order for people to use a beauty device, there was the hassle of having to visit a hospital with a dermatologist or a beauty shop. However, recently, as portable or relatively small beauty devices has been released, an environment in which people can easily use beauty devices at home is being created.

On the other hand, since beauty devices are manufactured differently depending on their uses, there is an inconvenience that people have to purchase beauty devices for each use. For example, people have to separately purchase a beauty device for scalp care, a beauty device for skin care, a beauty device for wrinkle improvement, etc., which increases the purchase cost, requires a large space for storage, and may experience inconveniences that are cumbersome to manage. Accordingly, users' needs for an integrated beauty device for scalp care, skin care, and the like are increasing.

Meanwhile, the beauty device integrated to be usable in various areas such as the scalp, skin, and the like has a limit of not being able to provide various functions. Specifically, there may be constraints on size and structure in that the beauty device is manufactured to be applicable to various areas. Therefore, for example, when the beauty device cares for the scalp, it is difficult to provide a massage function and a tonic absorption function at the same time, and even though the plurality of functions are provided at the same time, there is a limit that the effect thereof is low.

SUMMARY

Technical Problem

The present disclosure is directed to providing a beauty device capable of caring various areas, and to effectively providing various functions during scalp care.

The present disclosure is directed to providing a massage function and a tonic absorption function at the same time, and to improve efficiency of each of the functions.

Technical Solution

A beauty device according to an embodiment of the present disclosure may include a main body and a head module detachable from the main body, wherein the head module may include at least one of a plurality of protrusions, a light-emitting part, an electrode part, a sensor, and a motor, and the sensor may include a proximity sensor.

The plurality of protrusions may be disposed along at least one virtual circle, and the light-emitting part may be disposed around the plurality of protrusions.

The electrode part and the sensor may be disposed inside the virtual circle.

The proximity sensor may be one or more, the electrode part may include a plurality of electrodes, and the proximity sensor may be disposed between the plurality of electrodes.

The light-emitting part, the electrode part, and the motor may operate when the proximity sensor detects an object within a predetermined distance.

A height of the electrode part may be lower than a height of each of the plurality of protrusions.

Each of the plurality of protrusions may have a truncated cone shape in which a diameter of an upper surface thereof is smaller than a diameter of a lower surface thereof.

The head module may include an operation part including a base in which the plurality of protrusions, a light-emitting part, an electrode part, and a sensor are disposed on one surface thereof and a connection part connected to the main body, and an area occupied by the plurality of protrusions in the base may be larger than an area occupied by the light-emitting part in the base.

A ratio of the area occupied by the plurality of protrusions to an entire area of the base may be 2 to 10%, and a ratio of the area occupied by the light-emitting part to the entire area of the base may be 2 to 5%.

The motor may be disposed on the other surface of the base.

The plurality of protrusions may be formed of rubber, urethane, or silicone.

Advantageous Effects

According to an embodiment of the present disclosure, the beauty device can be used for a plurality of areas such as the face and the scalp, and there is an advantage that a plurality of functions are effectively provided for each area.

According to an embodiment of the present disclosure, there is an advantage that the absorption of the scalp ampoule and the like can be promoted by providing a massage effect through the plurality of protrusions and evenly transmitting light to the scalp through the light-emitting part disposed around the protrusions.

According to an embodiment of the present disclosure, the problem of misrecognition of the sensor is minimized as the sensor is disposed closer to the center rather than the outer circumference of the head module, thereby the light-emitting part, the electrode part, or the motor operates only when the beauty device is in use, and thus there is an advantage that power consumption is reduced and the inconvenience that light emitted by the light-emitting part reaches the user's eyes and the like is minimized.

According to an embodiment of the present disclosure, there is an advantage that a vibration transfer rate in a protrusion direction is improved by a shape of the protrusion, the arrangement of the motor, and the like.

DETAILED DESCRIPTION OF THE EMBODIMENTS

Figure 1:
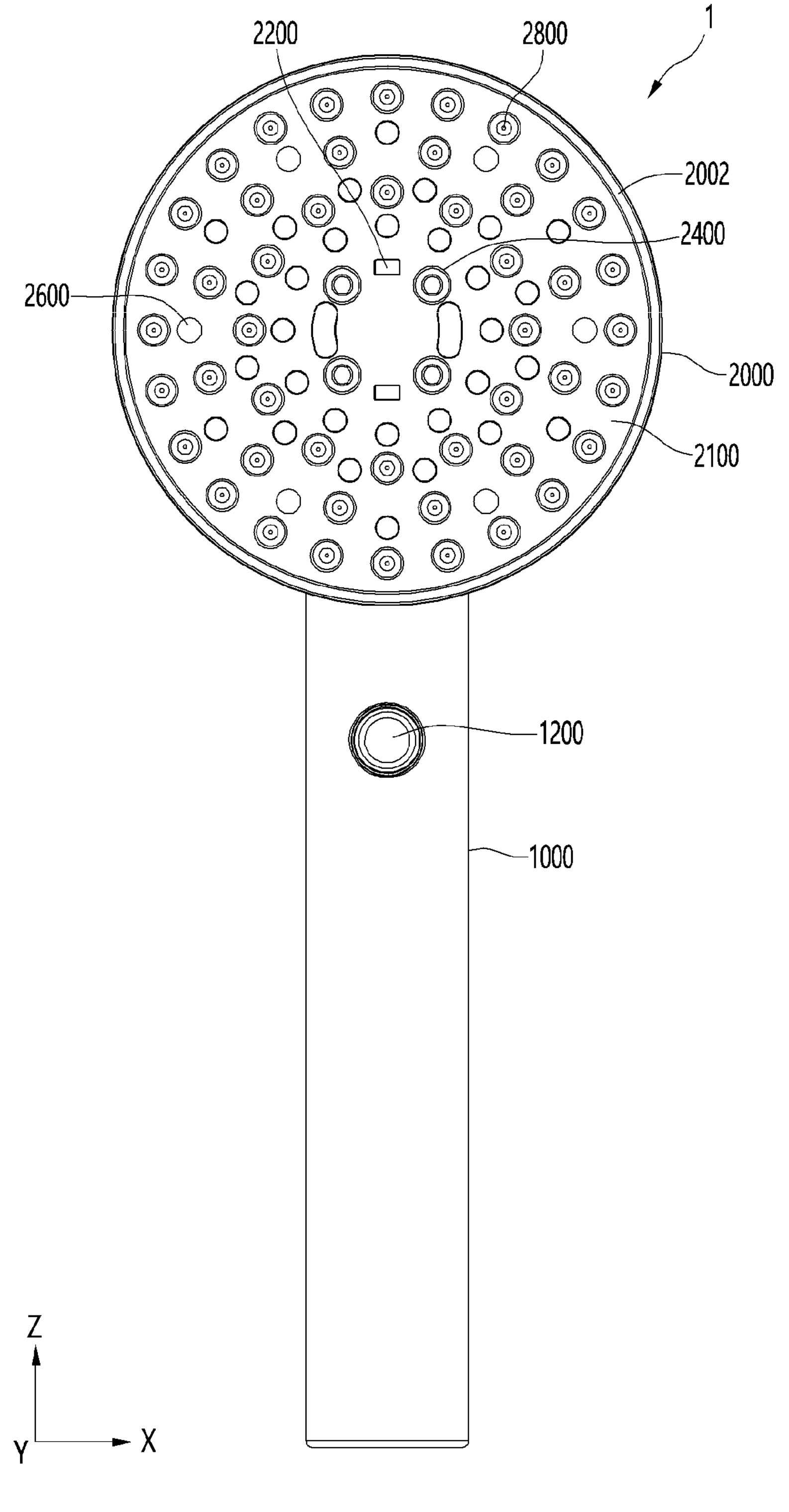
FIG. 1 is a front view of a beauty device according to an embodiment of the present disclosure.

Hereinafter, embodiments disclosed in the present specification will be described in detail with reference to the accompanying drawings, however, the same elements are designated by the same reference numerals, and repeated description thereof will be omitted.

Suffixes "module" and "part" for elements used in the following descriptions are given or used just for convenience in writing the specification, and do not have meanings or roles distinguishable between them.

In addition, in describing embodiments of the present disclosure, when detailed description of a known function is deemed to unnecessarily blur the gist of the present disclosure, the detailed description will be omitted. Further, accompanying drawings are only for easily understanding embodiments disclosed in the present disclosure, and the technical spirit disclosed in the present disclosure are not limited by the accompanying drawings, and it should be understood that the present invention includes all modifications, equivalents, and alternatives falling within the spirit and scope of the claims.

The terms including an ordinal number such as first, second, and the like may be used to describe various elements, but the elements are not limited by the terms. The terms are only used to distinguish one element from another.

The singular expression includes the plural expression unless the context clearly dictates otherwise.

It should be understood that the terms such as "comprises", "have", or the like, when used in the present application, specify the presence of stated features, integers, steps, operations, elements, and/or components, but do not preclude the presence or addition of one or more other features, integers, steps, operations, elements, components, and/or groups thereof.

FIG. 1 is a front view of a beauty device according to an embodiment of the present disclosure.

A beauty device 1 according to an embodiment of the present disclosure may include a main body 1000 and a head module 2000.

The main body 1000 may be formed in a cylindrical shape. The main body 1000 may be a handle of a beauty device 1. In this case, the feeling of grip may be improved. Meanwhile, the shape of the main body 1000 is merely an example, and thus it is appropriate that the present disclosure is not limited thereto. That is, the main body 1000 may have a shape that is easy for a user to grip by hand, for example, a bar or stick shape extending in one direction, such as a polygonal pole, or the like. Accordingly, the user may easily control a position of the beauty device 1 by gripping the main body 1000 by hand.

The main body 1000 may include an accommodating space (not shown) therein. A battery (not shown) may be disposed in the accommodating space of the main body 1000. The battery may supply power to the beauty device 1. For example, the battery may supply power to the main body 1000 and the head module 2000 connected to the main body 1000, respectively. The battery may include one selected from primary batteries such as a manganese (Mn) battery, an alkaline battery, a mercury battery, a silver oxide battery, and the like. In addition, the battery may include one selected from secondary batteries such as a nickel cadmium (Ni—Cd) battery, a nickel hydride (Ni-MH) battery, a lithium ion (Li-ion) battery, and the like.

When the beauty device 1 includes a rechargeable battery, a cover (not shown) for attaching and detaching the battery may be disposed on the outside of the main body 1000. Alternatively, when the battery is disposed inside the main body 1000 and it is difficult to attach or detach, the beauty device 1 may include a charging terminal part (not shown). The charging terminal part may be electrically connected to the battery disposed inside the main body 1000, and a part thereof may be exposed to the outside of the main body 1000 (e.g., a lower surface of the main body 1000). The user may connect a USB port, a cable, or the like for charging the battery to the exposed charging terminal to charge the battery. Still alternatively, the beauty device 1 may be provided to enable wireless charging. In detail, the beauty device 1 may be provided to be wirelessly charged by a coil disposed in the main body 1000. For example, the beauty device 1 may charge the battery using a wireless charging method such as a magnetic resonance method, a magnetic induction method, or the like.

At least one button 1200 may be disposed outside the main body 1000. The beauty device 1 may receive a user command through the button 1200. The button 1200 may be a button for turning on or off the power of the beauty device 1, but this is merely an example.

The button 1200 may be a physical switch including an elastic body such as a spring, or the like. In addition, the button 1200 may be an electrical switch in which a touch electrode or the like is formed. The user may control the beauty device 1 through the button 1200.

In addition, an indicator lamp (not shown) may be disposed outside the main body 1000. For example, the indicator lamp may be disposed adjacent to the button 1200. The indicator lamp may indicate a state of the beauty device. For example, when the user operates the beauty device 1 through the button 1200 (On mode), the indicator lamp may emit light with a set color. In addition, when the user terminates an operation of the beauty device 1 through the button 1200 or the operation of the beauty device 1 is terminated by a set time (off mode), the indicator lamp may not emit light or may emit light of a different color from light of the On mode.

A speaker (not shown) may be disposed in the accommodation space of the main body 1000. The speaker may output a state of the beauty device 1 as a sound. For example, when the user operates the beauty device 1 through the button 1200 (On mode), the speaker may output a sound indicating the start of operation. In addition, when the operation of the beauty device 1 is terminated (off mode), the speaker may output a sound for the end of the operation.

The head module 2000 shown in FIG. 1 may be an example of a module for taking care of the scalp. The head module 2000 may include at least one sensor 2200, at least one electrode part 2400, at least one light-emitting part 2600, and at least one protrusion 2800. Meanwhile, according to an embodiment, at least one of the sensor 2200, the electrode part 2400, the light-emitting part 2600, the protrusion 2800, a motor 2900 (see FIG. 7), and a processor 3000 (see FIG. 7) may be omitted or other components may be further included.

The sensor 2200 may detect whether the beauty device 1 is used. Specifically, even when the user is not using the beauty device 1, while the power of the beauty device 1 is turned on, the electrode part 2400, the light-emitting part 2600, or the motor 2900 continues to operate, problems such as unnecessary power consumption and irradiating light to an arbitrary area may occur. Therefore, the processor 3000 may drive the electrode part 2400, the light-emitting part 2600, or the motor 2900 only when it is detected that the beauty device 1 is being used through the sensor 2200.

According to an embodiment, the sensor 2200 may be a proximity sensor. The type of the proximity sensor may be various. For example, the proximity sensor may include a combination of a permanent magnet and a Hall element whose internal current changes due to the influence of magnetism, a combination of a lamp or a light-emitting diode and an optical sensor, detection of changes in electrostatic capacity, and the like.

The sensor 2200 may detect whether an object (e.g., scalp) is positioned within a predetermined distance. The predetermined distance may be 3 cm, but since this is merely an example, it is appropriate that the present disclosure is not limited thereto.

When the object is positioned within the predetermined distance through the sensor 2200, the processor 3000 may recognize that the beauty device 1 is in use, and when the object is not positioned within the predetermined distance, the processor 300 may recognize that the beauty device 1 is not in use.

Meanwhile, the type of the sensor 2200 may be various. Specifically, the sensor 2200 may be a sensor other than the proximity sensor.

The electrode part 2400 may output a micro current. For example, the electrode part 2400 may include four electrodes, and in this case, two of the four electrodes may be anodes, and the remaining two may be cathodes.

The light-emitting part 2600 may output light. For example, the light-emitting part 2600 may include at least one of an Infrared (IR) module, an LED module, and a laser module. Therefore, the light-emitting part 2600 may output at least one of IR, red light, and laser. The IR module may output infrared, and the LED module may output red light in a wavelength band of about 620 nm to about 750 nm. The laser module may include a laser diode and output a laser.

Meanwhile, the head module 2000 may include a connection part 2001 (see FIG. 2) connected to the main body 1000 and an operation part 2002 (see FIG. 2) coupled to the connection part 2001.

The operation part 2002 may be a configuration for performing scalp care. The operation part 2002 may include a base 2100, and one surface of the base 2100 may be a surface facing the user's scalp when the beauty device 1 is used.

The sensor 2200, the electrode part 2400, the light-emitting part 2600, or the protrusion 2800 may be formed on one surface of the base 2100. The base 2100 may support the sensor 2200, the electrode part 2400, the light-emitting part 2600, or the protrusion 2800.

The protrusion 2800 may be formed to protrude from the base 2100 and may apply pressure to the scalp or the like. The protrusion 2800 may be formed of a material having elasticity, such as rubber, urethane, silicone, or the like. In addition, when the protrusion 2800 is formed of the same material as described above, it is possible to effectively transmit the vibration force to the scalp.

The motor 2900 may vibrate the head module 2000. In particular, the motor 2900 may vibrate the protrusion 2800 formed to protrude from the base 2100. The motor 2900 may be disposed on the other surface of the base 2100.

The processor 3000 may control the operation of the beauty device 1. In detail, the processor 3000 may control each of the sensor 2200, the electrode part 2400, the light-emitting part 2600, the protrusion 2800, and the motor 2900.

Meanwhile, the head module 2000 may be attached to and detached from the main body 1000. That is, the head module 2000 may be separated from the main body 1000. A diagnosis module, a skin care module, or an ampoule care module as well as the head module 2000 may be mounted on the main body 1000.

Figure 2:
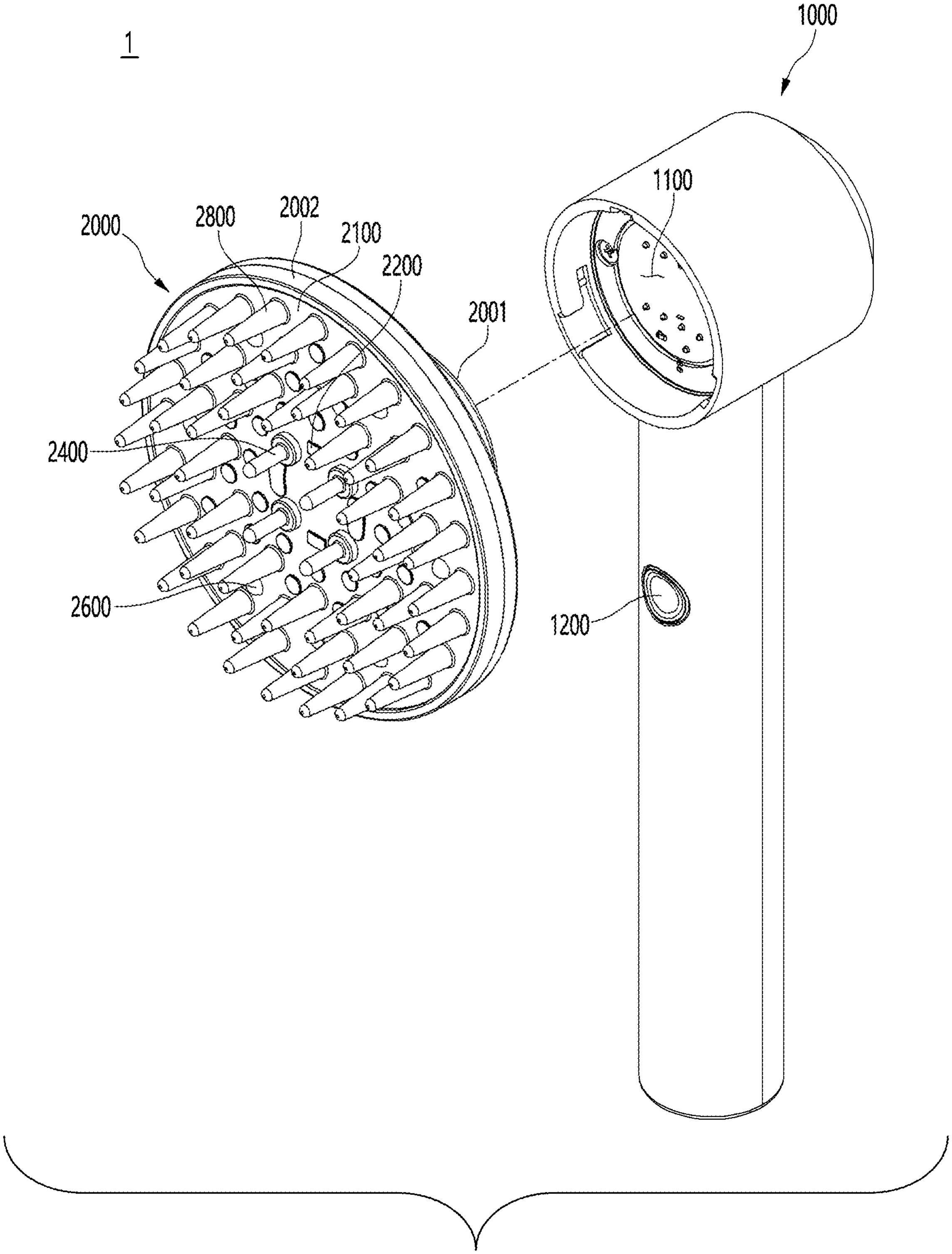
FIG. 2 is a perspective view illustrating a state in which a head module and a main body are separated according to an embodiment of the present disclosure.
Figure 3:
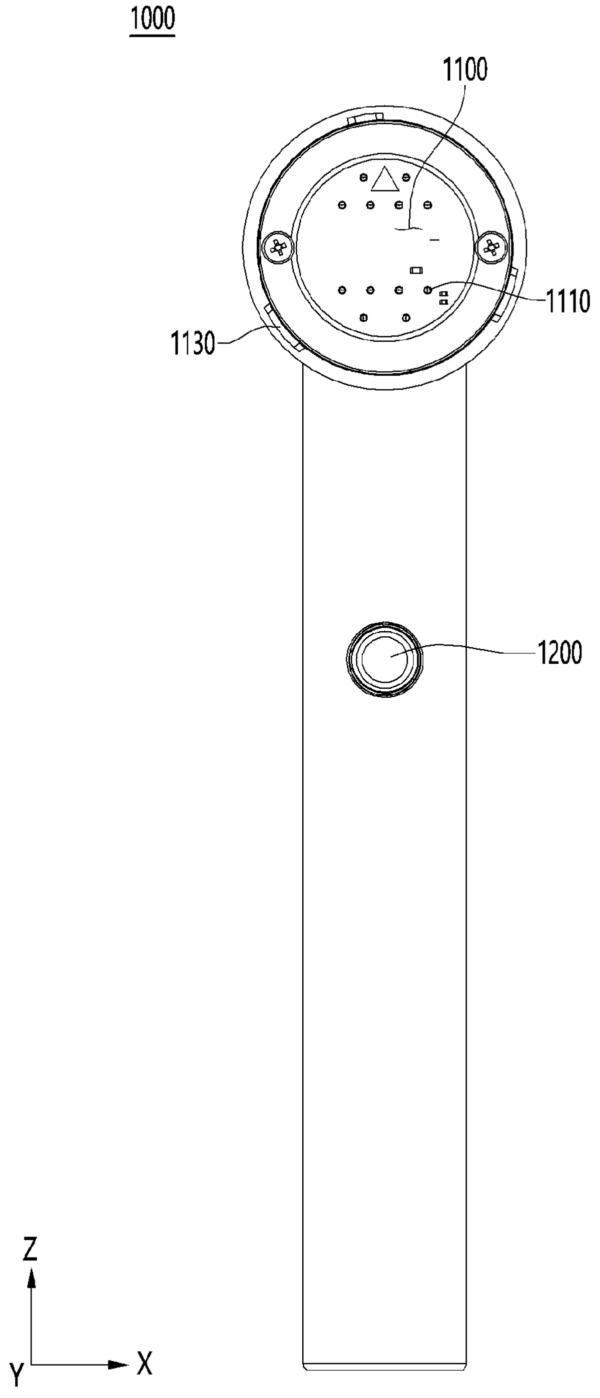
FIG. 3 is a front view illustrating the main body of FIG. 2.
Figure 4:
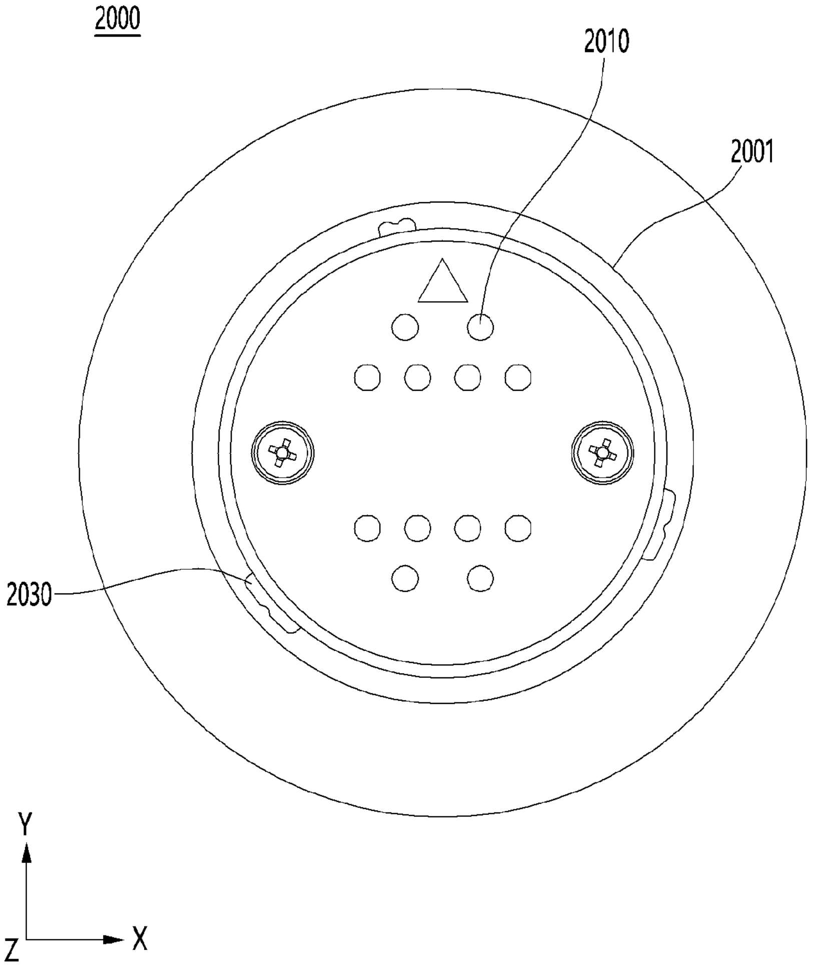
FIG. 4 is a rear view of the head module shown in FIG. 2.

FIG. 2 is a perspective view illustrating a state in which the head module and the main body are separated according to an embodiment of the present disclosure, FIG. 3 is a front view illustrating the main body of FIG. 2, and FIG. 4 is a rear view of the head module shown in FIG. 2.

The head module 2000 may include the connection part 2001 to be coupled to the main body 1000 and the operation part 2002 for caring the user's scalp.

A recess 1100 for mounting the head module 2000 may be formed in the main body 1000, and the connection part 2001 formed in the head module 2000 may be coupled to the main body 1000.

The recess 1100 may be formed on one side of the main body 1000. The recess 1100 may have a concave shape from one side of the main body 1000 toward the inside of the main body 1000.

The main body 1000 may include at least one first terminal 1110. The first terminal 1110 may be disposed on a lower surface of the recess 1100. The first terminal 1110 may be electrically connected to a battery disposed in the main body 1000.

In addition, at least one groove 1130 may be formed in the recess 1100. The groove 1130 may be disposed on an inner circumferential surface of the recess 1100. The groove 1130 may have a concave shape from the inner circumferential surface toward an outer circumferential surface of the recess 1100.

The main body 1000 may be connected to the head module 2000. The main body 1000 may be physically connected to the head module 2000. For example, the recess 1100 of the main body 1000 may have a shape corresponding to the connection part 2001 of the head module 2000 and may be provided with a predetermined depth corresponding to the connection part 2001. Accordingly, a part of the head module 2000, that is, the connection part 2001 may be inserted into the recess 1100 to be connected to the main body 1000.

At least one protrusion portion 2030 may be formed in the head module 2000. The protrusion portion 2030 may be disposed on an outer surface of the head module 2000. The protrusion portion 2030 may be disposed in a region corresponding to the groove 1130 of the main body 1000. In addition, the number of protrusions 2030 may correspond to the number of grooves 1130. The head module 2000 may be physically connected by inserting the protrusion portion 2030 into the groove 1130.

In addition, the head module 2000 may be electrically connected to the main body 1000. For example, at least one second terminal 2010 disposed on a lower surface facing the lower surface of the recess 1100 may be formed in the head module 2000. The second terminal 2010 may be disposed in an area corresponding to the first terminal 1110 and may be in contact with the first terminal 1110. In detail, the second terminal 2010 may be in contact with the first terminal 1110 in a process of physically coupling the head module 2000 and the main body 1000, for example, physically coupling the protrusion portion 2030 and the groove 1130. Accordingly, the first terminal 1110 may be electrically connected to the second terminal 2010, and the main body 1000 and the head module 2000 may be electrically connected to each other. Therefore, the battery disposed in the main body 1000 may supply power to the head module 2000.

The battery disposed in the main body 1000 may supply power to the sensor 2200, the electrode part 2400, the light-emitting part 2600, the motor 2900 (see FIG. 7), the processor 3000 (see FIG. 7), or the like in the head module 2000. The sensor 2200, the electrode part 2400, the light-emitting part 2600, the motor 2900 (see FIG. 7), the processor 3000 (see FIG. 7), or the like may receive the power from the battery disposed in the main body 1000 to operate individually.

Next, the sensor 2200, the electrode part 2400, the light-emitting part 2600, the protrusion 2800, the motor 2900 (see FIG. 7) and the processor 3000 (see FIG. 7), or the like constituting the head module 2000 will be described in detail.

Figure 5:
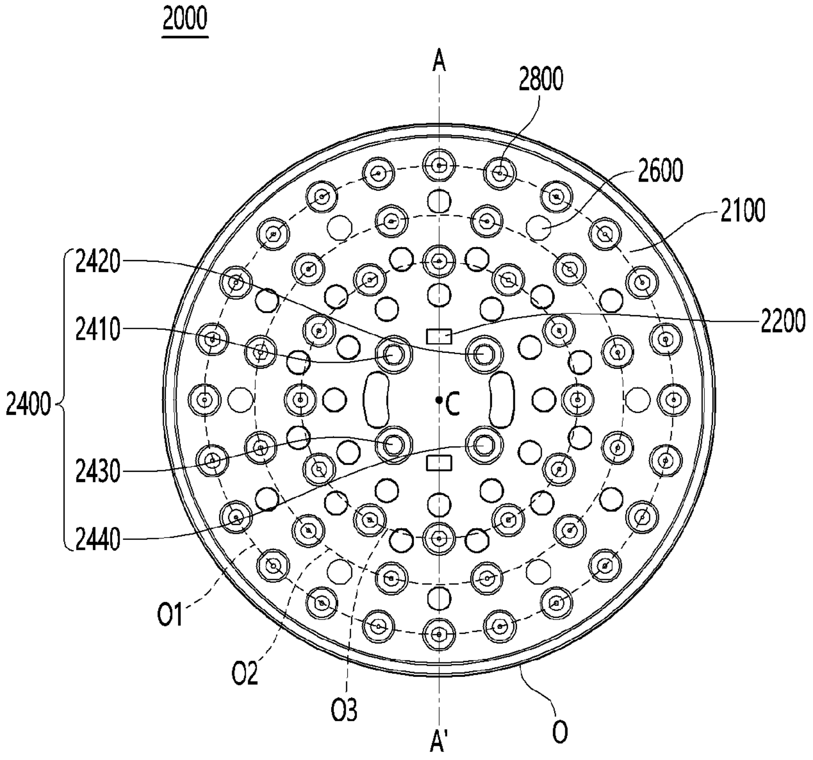
FIGS. 5 to 6 are front views of the head module according to an embodiment of the present disclosure.
Figure 6:
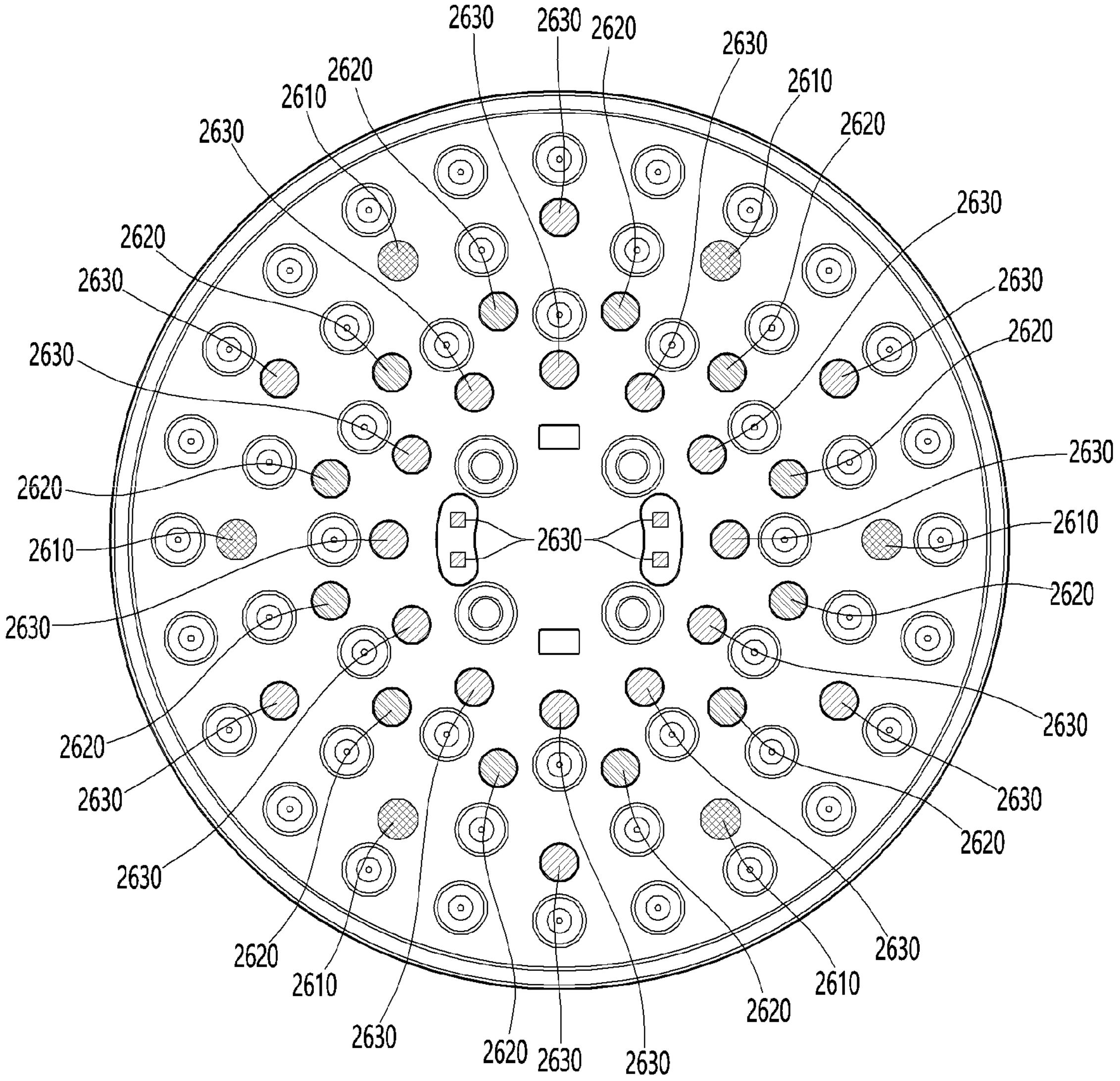
Figure 7:
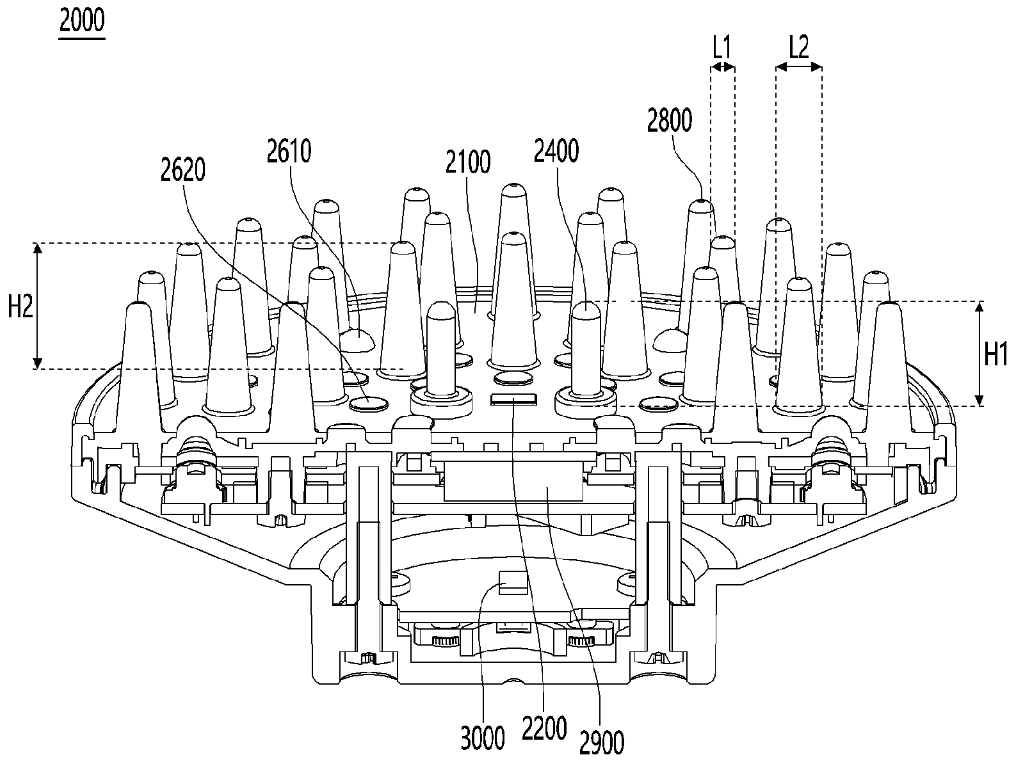
FIG. 7 is a view illustrating the head module, which is assumed to be taken along line A-A' in FIG. 5.
Figure 8:
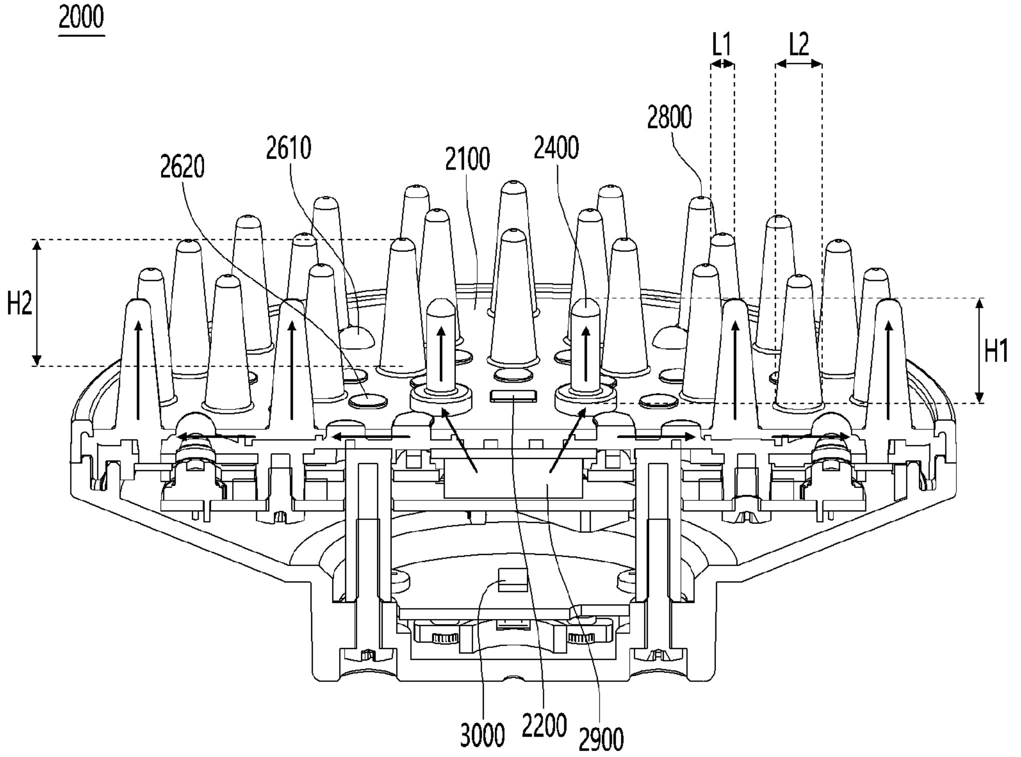
FIG. 8 is a view illustrating a direction in which vibration force is transmitted by driving a motor in FIG. 7.

FIGS. 5 to 6 are front views of the head module according to an embodiment of the present disclosure, FIG. 7 is a view illustrating the head module assumed to be taken along line A-A' in FIG. 5, and FIG. 8 is a view illustrating a direction in which a vibration force is transmitted by driving a motor in FIG. 7.

At least one sensor 2200 may be provided in the head module 2000. The sensor 2200 may be one or in plural.

The sensor 2200 may be disposed closer to the center C than the outer circumference O of the head module 2000. Specifically, the sensor 2200 may be disposed inside the plurality of protrusions 2800 and the light-emitting part 2600. As such, when the sensor 2200 is disposed close to the center C of the head module 2000, a problem of misrecognition may be minimized compared to when the sensor 2200 is disposed close to the outer circumference O of the head module 2000. Specifically, even when the beauty device 1 is not in use, a case may occur that a part of the head module 2000 is covered by other objects, etc. In particular, this case is because the probability of occurrence is higher on the outer circumference O side than the center C of the head module 2000.

The sensor 2200 may be in plural. When a preset number or more of sensors among the plurality of sensors 2200 detect an object within a predetermined distance, the processor 3000 may recognize that the beauty device 1 is in use.

That is, when there is one proximity sensor 2200 and one proximity sensor 2200 detects the object within the predetermined distance, the light-emitting part 2600, the electrode part 2400, and the motor 2900 may operate, and when the proximity sensor 2200 is in plural and the preset number or more of sensors among the plurality of sensors detect the object within the predetermined distance, the light-emitting part 2600, the electrode part 2400, and the motor 2900 may operate.

The electrode part 2400 may include first to fourth electrodes 2410, 2420, 2430, and 2440. The electrode part 2400 may be formed of a material harmless to the human body. The electrode part 2400 may not be deformed by pressure in contact with the skin and may include a conductive metal material. As an example, the electrode part 2400 may include at least one of aluminum (Al), copper (Cu), zinc (Zn), iron (Fe), nickel (Ni), chromium (Cr), silver (Ag), gold (Au), and platinum. (Pt), stainless steel (SUS), and alloys thereof.

The electrode part 2400 may be in contact with the user's skin. The electrode part 2400 may provide at least one of a high-frequency current, a galvanic current, and a microcurrent to the user's skin.

Two of the first to fourth electrodes 2410, 2420, 2430, and 2440 may be positive electrodes, and the other two may be negative electrodes.

Similar to the sensor 2200, the electrode part 2400 may be disposed closer to the center C than the outer circumference O of the head module 2000.

According to an embodiment, the electrode part 2400 may be alternately disposed with the sensor 2200. For example, the sensor may be disposed between the electrode and the electrode, and the electrode may be disposed between the sensor and the sensor.

The light-emitting part 2600 may be disposed between the sensor 2200 and the outer circumference O or between the electrode part 2400 and the outer circumference O. The light-emitting part 2600 may be formed around the plurality of protrusions 2800. The light-emitting part 2600 may be radially disposed from the center C toward the outer circumference O.

The plurality of protrusions 2800 may be disposed along at least one virtual circle. For example, the plurality of protrusions 2800 may be disposed along a first virtual circle O1, a second virtual circle O2, and a third virtual circle O3, but the number of virtual circles is merely an example. The first virtual circle O1 may be the largest, and the third virtual circle O3 may be the smallest. The second virtual circle O2 may be smaller than the first virtual circle O1 and may be larger than the third virtual circle O3.

The sensor 2200 and the electrode part 2400 may be disposed inside the third virtual circle O3.

The light-emitting part 2600 may be disposed between the plurality of protrusions 2800 disposed along the virtual circles O1, O2, and O3. The light-emitting part 2600 may be disposed around the plurality of protrusions 2800. The electrode part 2400 and the sensor 2200 may be disposed inside the virtual circles O1, O2, and O3.

The light-emitting part 2600 may be disposed between the first virtual circle O1 and the second virtual circle O2, between the second virtual circle O2 and the third virtual circle O3, or inside the third virtual circle O3, or the like. That is, the light-emitting part 2600 may be disposed around the plurality of protrusions 2800. The light-emitting parts 2600 may be arranged along concentric circles.

A hole may be formed in the base 2100 at a position corresponding to the light-emitting part 2600, and a light source may be disposed under the base 2100. Therefore, the light output from the light source may pass through the hole to reach the scalp. A lens may be disposed in each hole.

According to an embodiment, the light-emitting part 2600 may be divided into a first light-emitting part 2610, a second light-emitting part 2620, and a third light-emitting part 2630.

Referring to FIG. 6, the first light-emitting part 2610 may be a laser module. The first light-emitting part 2610 may be disposed between the first virtual circle O1 and the second virtual circle O2. The number of first light-emitting parts 2610 may be six, but this is merely an example. In the case of a low-power laser module, the light source has a characteristic of emitting light in a straight line. Accordingly, the first light-emitting part 2610 may be formed of a convex lens, and thus the laser may be evenly spread on the scalp through the convex lens.

The second light-emitting part 2620 may be an IR LED module. The second light-emitting part 2620 may be disposed along the third virtual circle O3. That is, the second light-emitting part 2620 may be disposed between the protrusions 2800 disposed along the third virtual circle O3. The number of second light-emitting parts 2620 may be twelve, but this is merely an example. Since the light source of the IR LED module has a wide angle of 120 degrees, the light source of the IR LED module may be irradiated over a wide area, and thus the second light-emitting part 2620 may be formed as a flat lens.

The third light-emitting part 2630 may be a red LED module. The third light-emitting part 2630 may be disposed between the first light-emitting parts 2610 or inside the third virtual circle O3. A part of the third light-emitting part 2630 may be disposed at a position that vertically overlaps the at least one sensor 2200. The number of third light-emitting parts 2630 may be twenty, but this is merely an example. Similarly, since the light source of the red LED module has a wide angle of 120 degrees, the light source of the red LED module may be irradiated over a wide area, and thus the third light-emitting part 2630 may be formed as a flat lens.

Meanwhile, the first light-emitting part 2610 is a laser module, the second light-emitting part 2620 is an IR LED module, and the third light-emitting part 2630 is a red LED module, but this is merely an example, and they may be changed from each other. That is, the first light-emitting part 2610 may be an IR LED module or a red LED module, the second light-emitting part 2620 may be a laser module or a red LED module, and the third light-emitting part 2630 may be a laser module or an IR LED module.

As described above, as a shape of the lens is formed differently according to the characteristics of each of the light-emitting parts 2600, light emitted from each light-emitting part may be efficiently transmitted to the scalp.

In addition, since the light-emitting part 2600 and the plurality of protrusions 2800 are disposed on a concentric basis and are formed of a flexible material, a position of the hair may be changed while pressing the scalp, and accordingly, it is possible to minimize a problem that the hair blocks the light emitted from each of the light-emitting part 2600.

Meanwhile, each of the plurality of protrusions 2800 may be spaced apart from each other at intervals of about 5 to 15 mm.

An area occupied by the plurality of protrusions 2800 in the base 2100 may be greater than or equal to an area occupied by the light-emitting part 2600 in the base 2100. Specifically, a ratio of the area occupied by the light-emitting part 2600 to the entire area of the base 2100 may be a first ratio, and a ratio of the area occupied by the plurality of protrusions 2800 to the entire area of the base 2100 may be the second ratio. The first ratio may be less than or equal to the second ratio.

Since the light emitted from the light-emitting part 2600 spreads to the surroundings, there is an advantage that it is possible to increase the massage performance and to evenly transmit the light to the scalp by increasing the ratio occupied by the protrusion 2800 rather than the ratio occupied by the light-emitting part 2600. For example, the first ratio may be 2 to 5%, and the second ratio may be 2 to 10%, but this is merely example, and thus it is appropriate that the present disclosure is not limited thereto.

Referring to FIG. 7, a height H1 of each of the first to fourth electrodes 2410, 2420, 2430, and 2440 may be lower than a height H2 of each of the protrusions 2800. When the height H1 of each of the first to fourth electrodes 2410, 2420, 2430, and 2440 is a first height and the height H2 of each of the protrusions 2800 is a second height, the first height may be lower than the second height. For example, the first height may be formed to be about 1 to 2 mm lower than the second height. As described above, when the protrusions 2800 are formed to be higher than the first to fourth electrodes 2410, 2420, 2430, and 2440, there is an advantage that pressure is evenly transmitted to the scalp.

The protrusion 2800 may have a circular truncated cone shape. A diameter L1 of an upper surface of the protrusion 2800 may be smaller than a diameter L2 of a lower surface thereof. The protrusion 2800 may be formed in a trapezoidal shape in the vertical cross section. Accordingly, the protrusion 2800 may be stably fixed to the base 2100 and evenly press the scalp. In addition, since the diameter L1 of the upper surface of the protrusion 2800 is smaller than the diameter L2 of the lower surface thereof, a frequency of the upper surface may be higher than that of the lower surface, and accordingly, a vibration force transmission effect may be increased.

In addition, in the head module 2000, the motor 2900 may be attached to the base 2100 in order to more efficiently transmit the vibration force to the protrusion 2800. As the protrusion 2800 is disposed on one surface of the base 2100 and the motor 2900 is disposed on the other surface of the base 2100, the vibration force generated in the motor 2900 may be transferred to the protrusion 2800, the electrode part 2400, and the like formed on the base 2100 along the base 2100. That is, the vibration generated in the motor 2900 may be transmitted to the protrusion 2800, the electrode part 2400, and the like along the arrow of FIG. 8.

As shown in FIG. 8, the vibration generated by the motor 2900 may move along the base 2100, and the vibration may again move along the protrusion 2800 fixed to the base 2100. Accordingly, the vibration may be effectively transmitted to the scalp.

Meanwhile, the processor 3000 or the like may be disposed inside the head module 2000. In addition, a substrate on which the processor 3000 is integrated may be disposed inside the head module 2000. The substrate may be a circuit board in which a circuit pattern is printed on an insulator. The substrate may include at least one of a resin material printed circuit board (PCB), a metal core PCB (MCPCB), a nonflexible PCB, a flexible PCB (FPCB), and a ceramic material. The substrate may include a resin material layer or a ceramic-based layer, and the resin material may be formed of silicone, an epoxy resin, a thermosetting resin including a plastic material, or a high heat resistance and high light resistance material. The ceramic material may include co-fired low temperature cofired ceramic (LTCC) or high temperature cofired ceramic (HTCC).

According to an embodiment of the present disclosure, the above-described method may be implemented as processor-readable code in a medium on which a program is recorded. Examples of the processor-readable medium include a ROM, a RAM, a CD-ROM, a magnetic tape, a floppy disk, an optical data storage, and the like.

The above-described descriptions are merely an example of the technological spirit of the present invention, and various modifications and variations may be made by those having ordinary skill in the art to which the present invention pertains without departing from the essential characteristics of the present invention.

Therefore, the embodiments disclosed in the present invention are not intended to limit the technological spirit of the present invention, but the embodiments are intended to describe, and the spirit and scope of the present invention is not limited by such embodiments.

The protection scope of the present invention should be construed by the following claims, and all technological spirits within the equivalent scope thereof should be construed as being included in the scope of right of the present invention.

What is claimed is:

1. A beauty device, comprising:

a main body; and a head module detachable from the main body, wherein the head module includes at least one of a plurality of protrusions, a light-emitting part, an electrode part, a sensor, and a motor, wherein the sensor includes a proximity sensor, wherein the light-emitting part includes:

a first light-emitting part disposed between a first virtual circle and a second virtual circle having a circumference less than a circumference of the first virtual circle, a second light-emitting part disposed along a third virtual circle having a circumference less than the circumference of the second virtual circle, and a third light-emitting part disposed inside the third virtual circle, wherein one of the first, second and third light-emitting parts is a laser module having a convex lens configured to compensate for a narrow collimated beam characteristic of laser light by diverging the laser beam to achieve even distribution across a scalp, wherein the others of the first, second and third light-emitting parts are an LED module having a flat lens configured to maintain a natural wide-angle emission characteristic of LED light for efficient area coverage, wherein the plurality of protrusions are disposed along the first, second and third virtual circles, wherein the electrode part and the sensor are disposed inside the third virtual circle, wherein the sensor is disposed closer to a center portion of the head module than to an outer circumference of the head module to minimize false detection caused by accidental covering of peripheral areas, wherein the light-emitting part, the electrode part, and the motor are configured to operate when the proximity sensor detects an object within a predetermined distance, and wherein an area occupied by the plurality of protrusions in a base of the head module is larger than an area occupied by the light-emitting part in the base, such that the plurality of protrusions are configured to displace hair to minimize interference with light transmission from the light-emitting part while simultaneously providing massage effects.

2. The beauty device of claim 1, wherein a height of the electrode part is lower than a height of each of the plurality of protrusions, such that the plurality of protrusions are configured to make initial contact with the scalp and distribute pressure evenly across the scalp before the electrode part contacts the scalp, thereby enabling simultaneous massage therapy and electrical therapy without creating pressure concentration points.

3. The beauty device of claim 1, wherein each of the plurality of protrusions has a truncated cone shape in which a diameter of an upper surface thereof is smaller than a diameter of a lower surface thereof, wherein the truncated cone shape creates an impedance gradient that increases vibration frequency toward the upper surface in contact with the scalp, and wherein the motor is disposed on a surface of the base opposite to the plurality of protrusions such that vibration from the motor transfers through the base to the plurality of protrusions and is amplified by the truncated cone shape for enhanced vibration transmission to the scalp.

4. The beauty device of claim 1, wherein the head module further includes:

an operation part including the base in which the plurality of protrusions, the light-emitting part, the electrode part, and the sensor are disposed on a first surface thereof; and a connection part connected to the main body, wherein the motor is disposed on a second surface of the base opposite to the first surface, wherein vibration generated by the motor travels along the base to the plurality of protrusions, to create a direct vibration transmission path that effectively delivers vibratory massage to the scalp, and wherein the area occupied by the plurality of protrusions in the base is larger than the area occupied by the light-emitting part in the base because light from the LED modules spreads at a wide angle, allowing fewer light sources while accommodating more protrusions for enhanced massage effect.

5. The beauty device of claim 4, wherein a ratio of the area occupied by the plurality of protrusions to an entire area of the base is 2 to 10%, and wherein a ratio of the area occupied by the light-emitting part to the entire area of the base is 2 to 5%.

6. The beauty device of claim 1, wherein the plurality of protrusions are formed of rubber, urethane, or silicone.

7. The beauty device of claim 1, wherein two of the plurality of protrusions are located closer to a center portion of the head module than two of the light-emitting parts.

8. The beauty device of claim 1, wherein the electrode part is located closer to a center portion of the head module than the plurality of protrusions, the light-emitting part and the sensor.

9. The beauty device of claim 1, wherein the light-emitting part is spaced apart from the plurality of protrusions on a face of the head module.

10. The beauty device of claim 1, wherein at least one of the plurality of protrusions is located closer to an adjacent protrusion of the plurality of protrusions than to the light-emitting part.

11. The beauty device of claim 1, wherein the electrode part includes four electrode parts configured to be located symmetrically to each other.

12. The beauty device of claim 11, wherein the sensor is located between two electrode parts of the four electrode parts.

13. The beauty device of claim 1, wherein the first light-emitting part is the laser module, wherein the second light-emitting part is an IR LED module, wherein the third light-emitting part is a Red LED module, and wherein the convex lens of the laser module has a divergence angle configured to spread laser light to cover an area comparable to areas covered by the LED modules despite the laser's inherently narrow beam.

14. The beauty device of claim 1, wherein the proximity sensor comprises at least one sensor, wherein the electrode part includes a plurality of electrodes symmetrically disposed, and wherein the proximity sensor is disposed between the plurality of electrodes to enable accurate proximity detection while avoiding electrical interference from the plurality of electrodes.

15. The beauty device of claim 1, wherein the plurality of protrusions are formed of an elastic material selected from rubber, urethane, and silicone, wherein the plurality of protrusions are configured to press and move hair on the scalp during use, creating gaps through which light from the light-emitting part penetrates to the scalp, and wherein a differential lens configuration including the convex lens and the flat lens ensures that both the laser light and the LED light effectively reach the scalp through the hair gaps created by the plurality of protrusions, thereby achieving a synergistic combination of massage and phototherapy effects.

16. The beauty device of claim 1, wherein the electrode part and the sensor are disposed inside the third virtual circle such that they are positioned in a central region of the head module, wherein positioning the electrode part centrally maximizes electrode-scalp contact despite hair interference, and wherein positioning the sensor centrally minimizes false activation by reducing exposure to accidental covering of the peripheral areas.

* * * * *